US012653612B2

(12) United States Patent (10) Patent No.: US 12,653,612 B2
Jeon et al. (45) Date of Patent: Jun. 16, 2026

(54) HEAT TREATMENT DEVICE AND APPARATUS AND METHOD FOR DETECTING ABNORMALITY THEREOF

(71) Applicant: ELECTRONICS AND TELECOMMUNICATIONS RESEARCH INSTITUTE, Daejeon (KR)

(72) Inventors: Soon Ik Jeon, Daejeon (KR); Wonyoung Song, Daejeon (KR); Kwang Jae Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 905 days.

(21) Appl. No.: 18/049,537

(22) Filed: Oct. 25, 2022

(65) Prior Publication Data

US 2023/0270495 A1 Aug. 31, 2023

(30) Foreign Application Priority Data

Feb. 28, 2022 (KR) ......................... 10-2022-0026361

(51) Int. Cl.
*A61B 18/18* (2006.01)
*A61B 18/00* (2006.01)
(52) U.S. Cl.
CPC .... *A61B 18/18* (2013.01); *A61B 2018/00898* (2013.01)

(58) Field of Classification Search
CPC ................ A61B 18/18; A61B 18/1815; A61B 2018/1876; A61B 2018/1823; A61N 5/02; A61N 5/022; A61N 5/025; A61N 1/403
See application file for complete search history.

(56) References Cited

U.S. PATENT DOCUMENTS 6,470,217 B1 10/2002 Fenn
8,306,628 B2 11/2012 Turner
10,328,289 B2 6/2019 Barthe
(Continued)

FOREIGN PATENT DOCUMENTS

JP 2015-171434 A 10/2015
KR 10-2017-0140734 A 12/2017
(Continued)

*Primary Examiner* — Ronald Hupczey, Jr.

(57) ABSTRACT

Provided are a heat treatment device and a method and apparatus for detecting an abnormality in the heat treatment. The heat treatment device includes a radio wave signal generator configured to generate target radio wave signals for heat treatment, a radio wave signal transmitter which includes an antenna configured to transmit the target radio wave signals to a body, a radio wave signal detector configured to detect the target radio wave signals from the antenna, a ratio information determiner configured to determine ratio information about a signal phase and a signal strength by comparing a reference target radio wave signal included in the detected target radio wave signals and each of the other target radio wave signals, and an abnormality occurrence determiner configured to determine whether an abnormality occurs in the heat treatment device based on the determined ratio information and predefined reference ratio information.

16 Claims, 5 Drawing Sheets

(56)            References Cited

U.S. PATENT DOCUMENTS

| 2008/0234574 | A1* | 9/2008 | Hancock | A61B 18/18 |
| | | | | 600/430 |
| 2014/0002056 | A1* | 1/2014 | Moul | G01R 23/00 |
| | | | | 324/76.39 |
| 2014/0012063 | A1* | 1/2014 | Turner | A61N 1/403 |
| | | | | 600/13 |
| 2018/0250522 | A1* | 9/2018 | Jeon | A61N 5/02 |
| 2018/0264281 | A1 | 9/2018 | Kim | |
| 2019/0111275 | A1 | 4/2019 | Jeon | |

FOREIGN PATENT DOCUMENTS

| KR | 10-2018-0079742 A | 7/2018 |
| KR | 10-2019-0042431 A | 4/2019 |

* cited by examiner

HEAT TREATMENT DEVICE AND APPARATUS AND METHOD FOR DETECTING ABNORMALITY THEREOF

CROSS-REFERENCE TO RELATED APPLICATION

This application claims the benefit of Korean Patent Application No. 10-2022-0026361 filed on Feb. 28, 2022, in the Korean Intellectual Property Office, the entire disclosure of which is incorporated herein by reference for all purposes.

BACKGROUND

1. Field of the Invention

One or more example embodiments relate to a heat treatment device and a technology which detects an abnormality of the heat treatment device.

2. Description of the Related Art

Treatment of diseases such as pain diseases and degenerative musculoskeletal diseases has mainly been treated with methods such as surgery, which has side effects such as pain and recurrence. As a technology which resolves such side effects, a non-invasive treatment is used which irradiates energy such as radio waves into the human body, converts the energy into heat, resulting in treatment. As an example of such a non-invasive treatment, there is a conventional technology which transmits a radio wave signal into the inner body with two antennas, generates heat in a lesion, and controls the heat generated by the radio wave signal by inserting a temperature detector for temperature monitoring into the body. However, conventional technology has a limitation in that it often malfunctions when transmitting radio wave signals during treatment. Therefore, research is needed to overcome this limitation.

SUMMARY

According to an aspect, there is provided a heat treatment device including a processor configured to generate target radio wave signals for heat treatment and a radio wave signal transmitter including an antenna which transmits the target radio wave signals to a body of a user. The processor may be configured to detect the target radio wave signals from the antenna, determine ratio information about a signal phase and a signal strength by comparing a reference target radio wave signal included in the detected target radio wave signals and each of the other target radio wave signals, and determine whether an abnormality occurs in the heat treatment device based on the determined ratio information and predefined reference ratio information.

The processor may generate an initial radio wave signal, distribute the initial radio wave signal into a plurality of radio wave signals, adjust a signal phase and a signal strength of each of the plurality of radio wave signals, and generate the target radio wave signals by amplifying the radio wave signals having the adjusted signal phase and the adjusted signal strength.

The processor may calculate the ratio information about the signal phase and the signal strength based on a signal phase and a signal strength of the reference target radio wave and a signal phase and a signal strength of each of the other target radio wave signals.

The processor may divide the reference target radio wave signal into a first reference target radio wave signal and a second reference target radio wave signal, shift a signal phase of the second reference target radio wave signal, calculate a first difference value which is a difference value between a half-wave signal phase and signal strength of the first reference target radio wave signal and a first half-wave signal phase and signal strength of the other target radio wave signals, calculate a second difference value which is a difference value between a half-wave signal phase and signal strength of the second reference target radio wave signal and a second half-wave signal phase and signal strength of the rest of the target radio wave signals, and calculate the ratio information based on the first difference value and the second difference value.

The processor may determine that an abnormality does not occur in the heat treatment device if it is determined that ratio information matches reference ratio information based on a predetermined reference.

The processor may determine that an abnormality occurs if it is determined that the ratio information does not match reference ratio information based on a predetermined reference.

The processor may correct a signal strength and a signal phase of the target radio wave signals if it is determined that the abnormality occurs.

The processor may provide an alarm for notifying about an occurrence of the abnormality of the heat treatment device and stop an operation of the heat treatment if it is determined that the abnormality occurs.

The target radio wave signals may include a plurality of radio waves which are controlled to different signal phases and signal strengths.

The processor may sequentially transmit the target radio wave signals which are detected by a radio wave signal detector to a ratio information determiner.

According to another aspect, there is provided a method of detecting an abnormality of a heat treatment device including generating target radio wave signals for heat treatment, detecting the target radio wave signals from an antenna which transmits the target radio wave signals to a body, determining ratio information about a signal phase and a signal strength by comparing a reference target radio wave signal included in the detected target radio wave signals and each of the other target radio wave signals, and determining whether an abnormality occurs in the heat treatment device based on the determined ratio information and predefined reference ratio information.

The generating of the target radio wave signal may include generating an initial radio wave signal, distributing the initial radio wave signal into a plurality of radio wave signals, adjusting a signal phase and a signal strength of each of the plurality of radio wave signals, and generating the target radio wave signals by amplifying the radio wave signals having the adjusted signal phase and the adjusted signal strength.

The determining of the ratio information may include calculating the ratio information about the signal phase and the signal strength based on a signal phase and a signal strength of the reference target radio wave and a signal phase and a signal strength of each of the other target radio wave signals.

The determining of the ratio information may include dividing the reference target radio wave signal into a first reference target radio wave signal and a second reference target radio wave signal, shifting a signal phase of the second reference target radio wave signal, calculating a first difference value which is a difference value between a half-wave signal phase and signal strength of the first reference target radio wave signal and a first half-wave signal phase and signal strength of the other target radio wave signals, calculating a second difference value which is a difference value between a half-wave signal phase and signal strength of the second reference target radio wave signal and a second half-wave signal phase and signal strength of the rest of the target radio wave signals, and calculating the ratio information based on the first difference value and the second difference value.

The determining of whether an abnormality occurs in the heat treatment device may include determining that an abnormality does not occur in the heat treatment device if it is determined that the ratio information about the signal phase and the signal strength of the target radio wave signals matches reference ratio information based on a predetermined reference.

The determining of whether an abnormality occurs in the heat treatment device may include determining that an abnormality occurs if it is determined that the ratio information about the signal phase and the signal strength of the target radio wave signals does not match reference ratio information based on a predetermined reference.

The method of detecting the abnormality of the heat treatment device may further include correcting a signal strength and a signal phase of the target radio wave signals if it is determined that the abnormality occurs.

The method of detecting the abnormality of the heat treatment device may further include providing an alarm for notifying the abnormality of the heat treatment device and stopping the operation of the heat treatment if it is determined that the abnormality occurs.

The target radio wave signals may include a plurality of radio waves which are controlled to different signal phases and signal strengths.

Additional aspects of example embodiments will be set forth in part in the description which follows and, in part, will be apparent from the description, or may be learned by practice of the disclosure.

According to example embodiments, a heat treatment device may detect and resolve malfunctions by itself, such as generation of high heat in an area other than the target area or generation of insufficient heat in the target area.

According to example embodiments, patients may be rid of pain, side effects, and others caused by conventional surgery by using a non-invasive treatment device which has a significantly low possibility of malfunction.

According to example embodiments, patients may be provided with safe and painless medical service.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
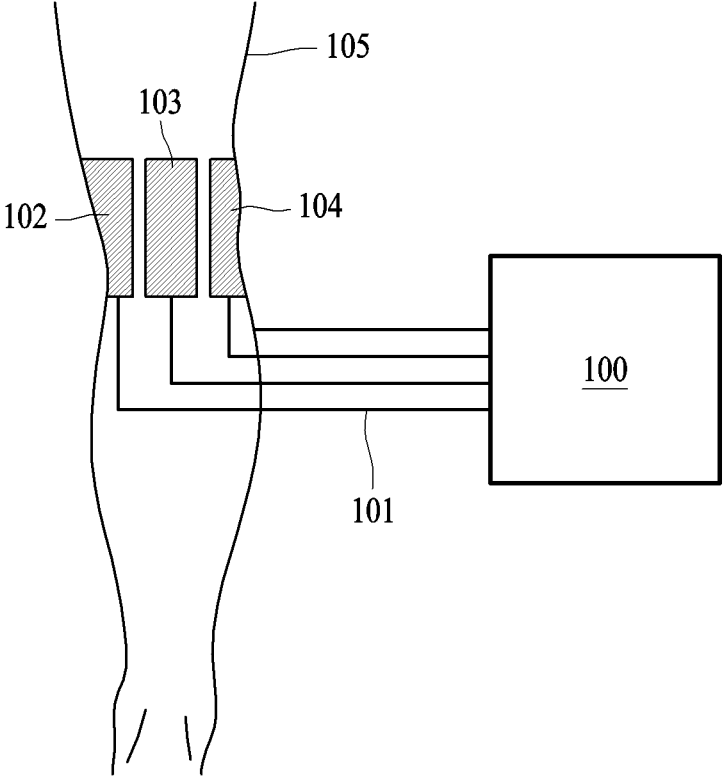
FIG. 1 is a schematic diagram describing the overall operation of a heat treatment device according to an example embodiment.

The following detailed structural or functional description is provided as an example only and various alterations and modifications may be made to the examples. Here, examples are not construed as limited to the disclosure and should be understood to include all changes, equivalents, and replacements within the idea and the technical scope of the disclosure.

Terms, such as first, second, and the like, may be used herein to describe various components. Each of these terminologies is not used to define an essence, order or sequence of a corresponding component but used merely to distinguish the corresponding component from other component(s). For example, a first component may be referred to as a second component, and similarly the second component may also be referred to as the first component.

It should be noted that if it is described that one component is "connected", "coupled", or "joined" to another component, a third component may be "connected", "coupled", and "joined" between the first and second components, although the first component may be directly connected, coupled, or joined to the second component.

The singular forms "a", "an", and "the" are intended to include the plural forms as well, unless the context clearly indicates otherwise. It will be further understood that the terms "comprises/including" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art and are not to be interpreted in an idealized or overly formal sense unless expressly so defined herein.

Hereinafter, example embodiments will be described in detail with reference to the accompanying drawings. When describing the example embodiments with reference to the accompanying drawings, like reference numerals refer to like elements and redundant descriptions related thereto will be omitted.

A heat treatment device described in the present disclosure may perform a method of detecting an abnormality which detects radio wave signals to be transmitted to the body during a non-invasive heat treatment for treating diseases such as pain diseases and degenerative musculoskeletal diseases, compares the radio wave signals with a reference radio wave signal, and determines whether an abnormality occurs in the heat treatment device based on the result of the comparison. The heat treatment device may determine the reference radio wave signal among radio wave signals, compare the signal phase and the signal strength of the reference radio wave signal with the signal phase and the signal strength of the rest of the radio wave signals except the reference radio wave signal and calculate the ratio information. The heat treatment device may compare the ratio information and the predetermined reference ratio information and detect whether an abnormality occurs in the heat treatment device based on the result of the comparison. The heat treatment device described herein may prevent malfunctions such as irradiating an area other than the target area with high heat or insufficient heat generated in the target area.

FIG. 1 is a schematic diagram describing an overall operation of a heat treatment device according to an example embodiment. Referring to FIG. 1, the heat treatment device 100 may generate target radio wave signals for heat treatment and transmit the generated target wave signals to antennas 102, 103, and 104 through a cable 101. The antennas 102, 103, and 104 may be attached to a body part 105 where the lesion of the user (or the patient) is located. The heat treatment device 100 may irradiate the body part 105 with target radio wave signals through the antennas 102, 103, and 104. The target radio wave signals are concentrated at the body part 105 by different signal phases and signal strengths, by which the heat treatment device 100 generates heat in the body.

The heat treatment device 100 may detect target radio wave signals from the antennas 102, 103, and 104 right before the target radio wave signals are transmitted into the body. The heat treatment device 100 may determine the reference target radio wave signal among target radio wave signals and determine the ratio information about the signal phase and the signal strength based on the signal phase and the signal strength of the rest of the target radio wave signals except for the reference target radio wave signals. The heat treatment device 100 may determine that an abnormality occurred in the heat treatment device 100 when there is a difference in value between the determined ratio information and the predetermined reference ratio information.

Figure 2:
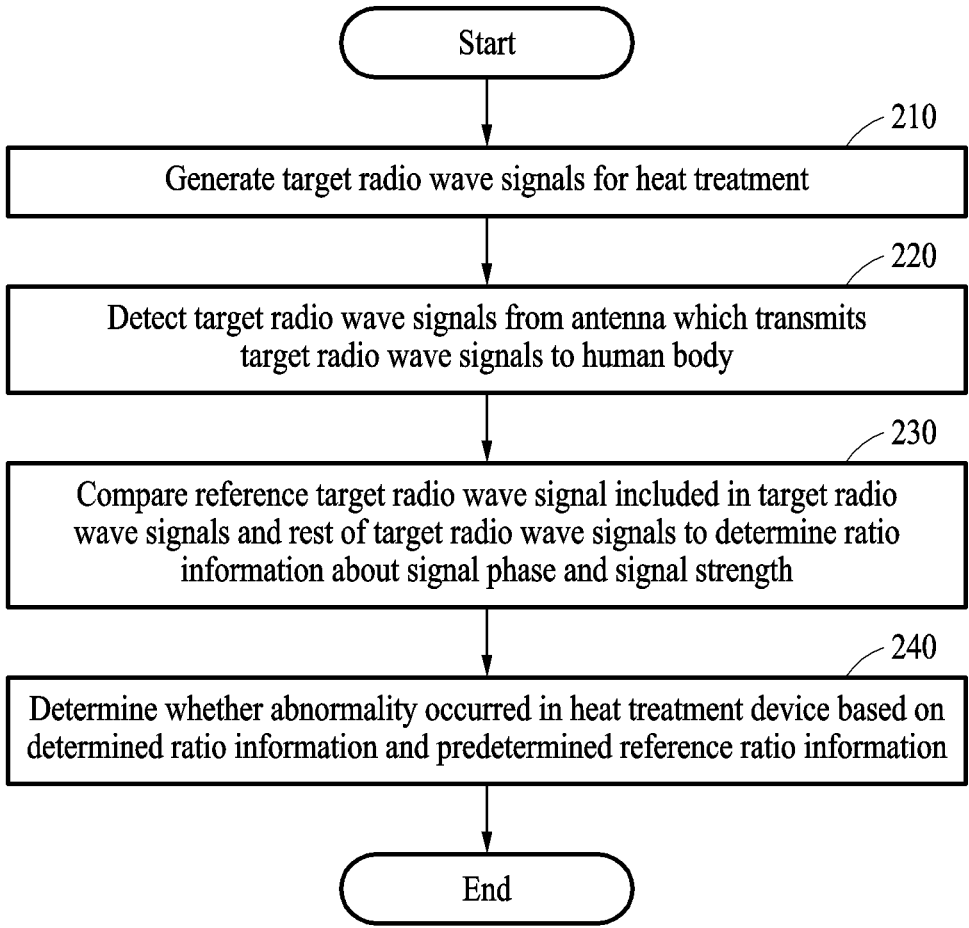
FIG. 2 is a flowchart describing an operation of a heat treatment device according to an example embodiment.

The heat treatment device and the method of detecting an abnormality performed by the heat treatment device is described in more detail through the example embodiments below. FIG. 2 is a flowchart describing an operation of a heat treatment device according to an example embodiment.

Referring to FIG. 2, the heat treatment device may generate target radio wave signals for heat treatment in operation 210. The heat treatment device may generate an initial radio wave signal. The initial radio wave signal may refer to, for example, a radio wave signal which is generated before the target radio wave signals. The heat treatment device may divide the initial radio wave signal into a plurality of radio wave signals. The heat treatment device may adjust a signal phase and a signal strength of each of the plurality of radio wave signals and generate the target radio wave signals by amplifying radio wave signals having the adjusted signal phase and the adjusted signal strength. The target radio wave signals may include a plurality of radio waves which are controlled to different signal phases and signal strengths. In operation 220, the heat treatment device may detect target radio wave signals from the antenna which transmits target radio wave signals to the body. The heat treatment device, for example, may detect the target radio wave signals right before the target radio wave signals are transmitted to the antenna.

In operation 230, the heat treatment device may determine the ratio information about the signal phase and the signal strength by sequentially comparing each of the reference target radio wave signal included in the detected target radio wave signals and the rest of the target radio wave signals. Each of the rest of the target radio wave signals may be compared with the reference target radio wave signal by switches. The heat treatment device in an example embodiment may calculate the ratio information about the signal phase and the signal strength based on the signal phase and the signal strength of the reference target radio wave and the signal phase and the signal strength of the rest of the target radio wave signals. The heat treatment device may calculate the ratio information about the signal phase based on the signal phase of the reference target radio wave and the signal phase of the rest of the target radio wave signals. Also, the heat treatment device may calculate the ratio information about the signal strength based on the signal strength of the reference target radio wave and the signal strength of the rest of the target radio wave signals.

In order to calculate the ratio information of the heat treatment device, the reference target radio wave signal may be divided into a first reference target radio wave signal and a second reference target radio wave signal. The heat treatment device may shift the signal phase of the second reference target radio wave signal and calculate a first difference value, which is a difference value between a half-wave signal phase and signal strength of the first reference target radio wave signal and a first half-wave signal phase and signal strength of the other target radio wave signals. The heat treatment device may calculate a second difference value which is a difference value between a half-wave signal phase and signal strength of the second reference target radio wave signal and a second half-wave signal phase and signal strength of the rest of the target radio wave signals. The heat treatment device may calculate the ratio information about the signal phase and the signal strength of the reference target radio wave signal and the rest of the target radio wave signals based on the first difference value and the second difference value.

In operation 240, the heat treatment device may determine whether an abnormality occurs in the heat treatment device based on the determined ratio information and predefined reference ratio information. For example, when it is determined that the ratio information about the signal phase and the signal strength of the target radio wave signals matches the reference ratio information based on the predetermined reference, the heat treatment device may determine that an abnormality did not occur in the heat treatment device. In contrast, when it is determined that the ratio information about the signal phase and the signal strength of the target radio wave signals does not match the reference ratio information based on the predetermined reference, the heat treatment device may determine that an abnormality occurred in the heat treatment device. When it is determined that an abnormality occurred, the heat treatment device may correct the signal phase and the signal strength of the target radio wave signals. That is, the heat treatment device may correct the signal phase and the signal strength of the target radio wave signals so that the ratio information may be determined to match the reference ratio information based on the predetermined reference. Also, if it is determined that an abnormality occurred, the heat treatment device may provide an alarm to notify that an abnormality occurred in the heat treatment device and stop the operation of the heat treatment. When it is determined that an abnormality occurred, the heat treatment device may provide alarms such as a warning sound so that the user may recognize the abnormality and handle it.

Figure 3:
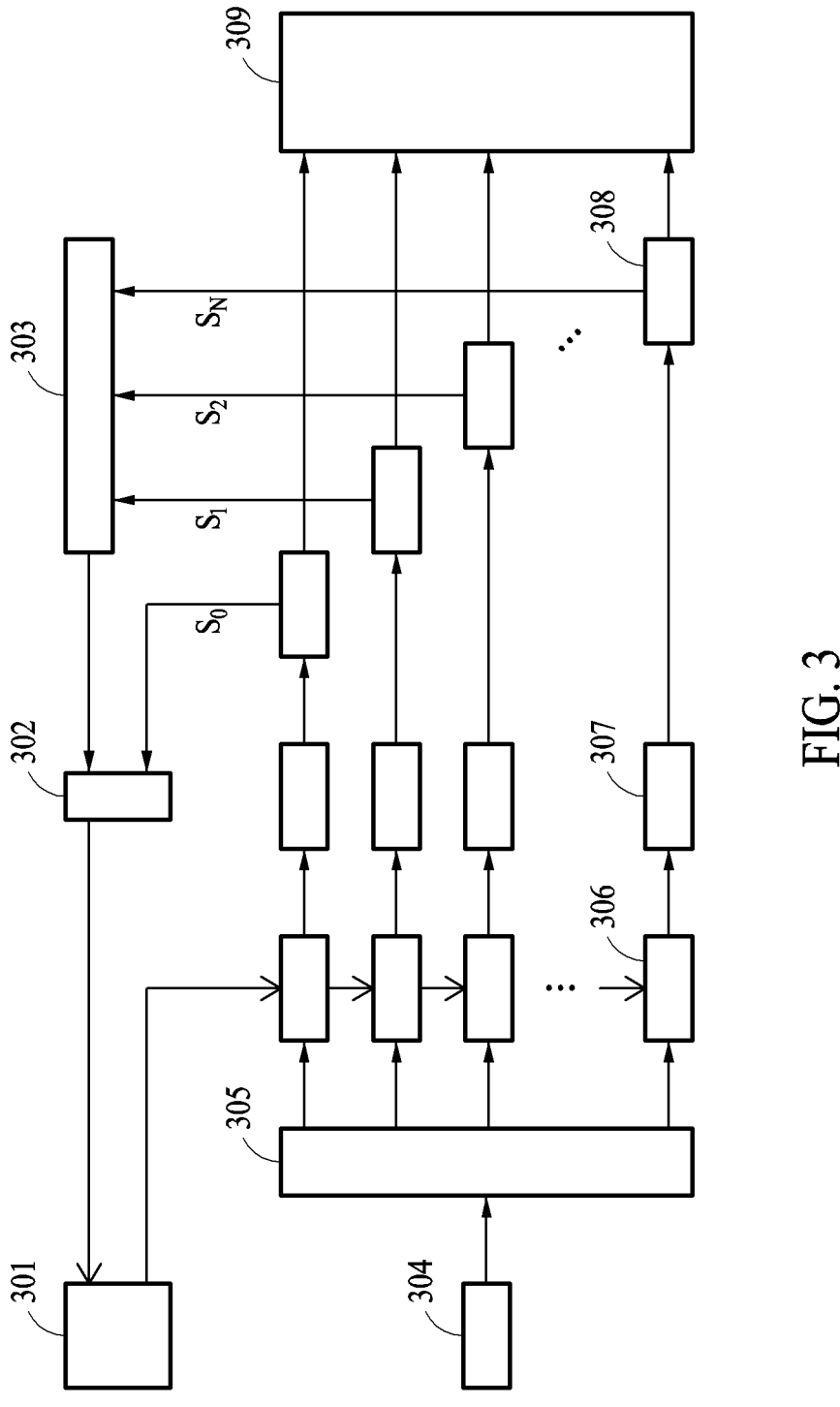
FIGS. 3 and 4 are diagrams illustrating a configuration of a heat treatment device which performs a method of detecting an abnormality according to an example embodiment.
Figure 4:
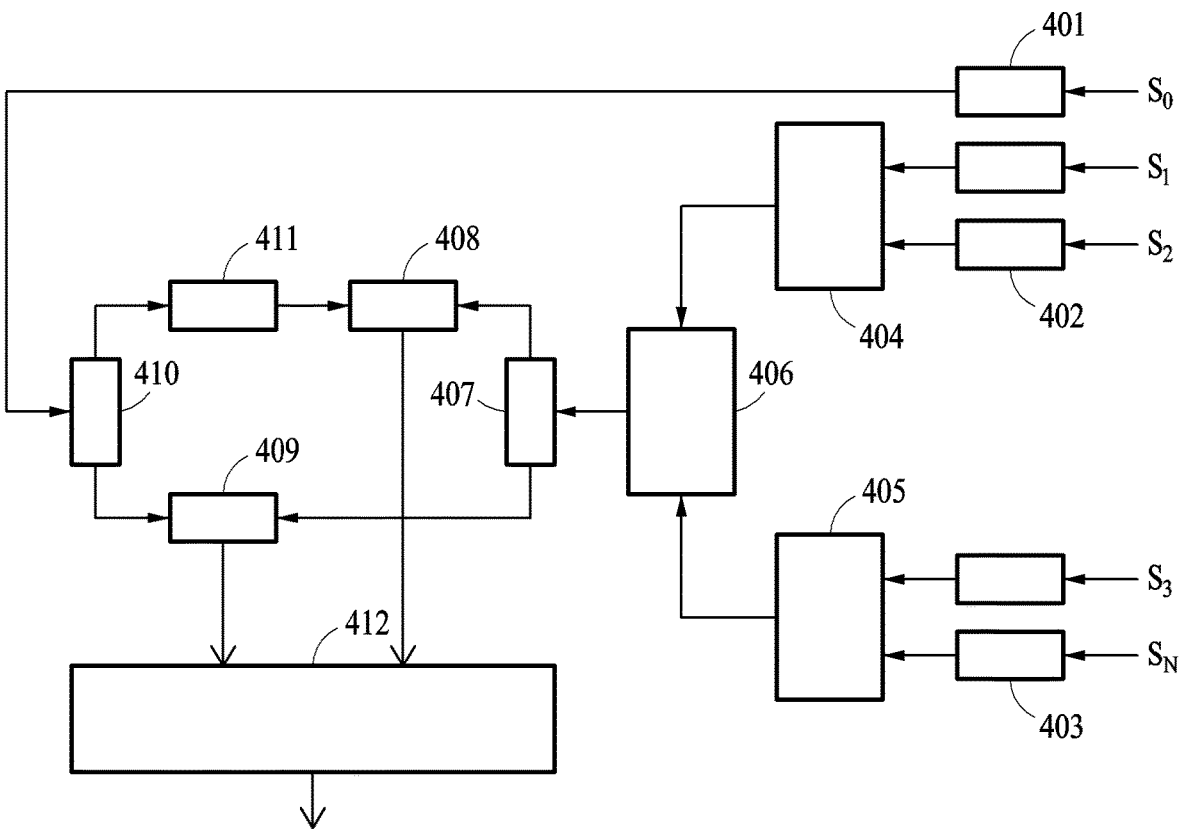

FIGS. 3 and 4 are diagrams illustrating a configuration of a heat treatment device which performs a method of detecting an abnormality according to an example embodiment.

Referring to FIG. 3, a radio wave signal generator 304 may generate initial radio wave signals for heat treatment.

The initial radio wave signals generated from the radio wave signal generator 304 may be divided into a plurality of radio wave signals in a transmission signal divider 305 and be transmitted to a number N (N is an integer greater than or equal to 1) of channel transceivers 306. The transmitted radio wave signals may be controlled in terms of signal phase and signal strength by the channel transceiver 306. The radio wave signals with controlled signal phase and signal strength may be amplified to a sufficient strength based on the predetermined reference by a radio wave output amplifier 307. The radio wave signals with controlled signal phase and signal strength may be transmitted to a detector 308. The detector 308 may include, for example, a directional combiner, and the detector 308 may pass the radio wave signals with controlled signal phase and signal strength through the directional combiner of the detector 308 to generate the target radio wave signals, which are number N of combined outputs. The number N of target radio wave signals may be transmitted to an exterior component 309 which includes an antenna. Here, the exterior component 309 may refer to components attached to the user's skin. The number N of combined outputs may be irradiated into the body where the lesion exists, through each antenna attached to the user skin. The number N of combined outputs may be expressed as, for example, S0, S1, S2, . . . . SN, and the outputs may be transmitted to components 301, 302, and 303 which detect radio wave signals and abnormalities.

The number N of combined outputs may pass the radio wave signal selector 303 and be transmitted to the radio wave signal comparator 302. The radio wave signal comparator 302 may sequentially compare the signal phase and the signal strength of N−1 target radio wave signals except for the reference target radio wave signal So and the reference target radio wave signal and transmit the difference value to the device logic circuit 301. The device logic circuit 301 may be a computer or a control device. The device logic circuit 301 may calculate relative ratio information about the signal phase and the signal strength of different target radio wave signals based on the difference value. The device logic circuit 301 may determine whether the calculated ratio information matches the reference ratio information. Here, the reference ratio information may be a predetermined relative ratio information of the signal phase and signal strength allocated to different target radio wave signals. The device logic circuit 301 may determine that the operation of the heat treatment device is normal if the reference ratio information and the calculated ratio information match and determine that the operation of the heat treatment device is abnormal if the reference ratio information and the calculated ratio information do not match. If the reference ratio information and the calculated ratio information do not match, the channel transceiver 306 may correct the signal phase and the signal strength. Or, if the reference ratio information and the calculated ratio information do not match, the device logic circuit 301 may perform a logic calculation operation which controls the entire device to run an alarm and an operation stopper.

The components 301, 302, and 303 which detect the radio wave signal and abnormalities in FIG. 3 will be illustrated in more detail in FIG. 4. The number N of combined outputs S0, S1, S2, . . . . SN are input to the component of FIG. 4, and the reference target radio wave signal So may pass an attenuator 401 and be divided into two sub-signals of the reference target radio wave signal through a divider 410. One of the sub-signals of the two reference target radio wave signals may be transmitted to a difference value detector 409 between the half-wave phase signal and the signal strength, and the other one may pass a 90 degree phase signal shifter 411 and be transmitted to a difference value detector 408 between the half-wave phase signal and the signal strength. The rest of the N−1 target radio wave signals except the reference target radio wave signal may pass the attenuators 402 and 403. Then, the rest of the N−1 target radio wave signals except the reference target radio wave signal may pass switches 404, 405, and 406 so the signals are selected sequentially. The target radio wave signals selected sequentially may be divided into sub-signals of two target radio wave signals through a divider 407. The sub-signals of the two target radio wave signals may each be transmitted to a difference value detector 408 and 409 between the half-wave phase signal and the signal strength. In one difference value detector 408 between the half-wave phase signal and the signal strength, the phase signal and signal strength of the rest of the N−1 target radio wave signals, except the reference target radio wave signal So which is 90 degrees phase signal delayed and the reference target radio wave signal, may be sequentially compared, and the difference value between the half-wave phase signal and the signal strength may be detected to be output by a difference value calculator 412 of the one wave signal and signal strength.

In the difference value detector 409 between the half-wave phase signal and signal strength, the rest of the N−1 target radio wave signals except the reference target radio wave signal So and the reference target radio wave signal may be compared in terms of phase signal and signal strength, and the difference value between the half-wave phase signal and the signal strength may be calculated. The difference value may be output from a difference value calculator 412 between the one wave phase signal and the signal strength, and the difference value calculator 412 between the phase signal and the signal strength may calculate the difference value between the phase signal and the signal strength with respect to the one wave reference target radio wave signal of the rest of the N−1 target radio wave signals except the reference target radio wave signal based on the two difference values, and transmit the information to the device logic circuit 301. The device logic circuit 301 in FIG. 3 may use the transmitted information to calculate the ratio information about the phase signal and the signal strength of the different number N of target radio wave signals. Also, the device logic circuit 301 may determine whether the ratio information about the detected number N of target radio wave signals matches the reference ratio information, which is the ratio information about the phase signal and the signal strength allocated for the control of initially different number N of radio wave signals. The operation may be determined as normal if the existing ratio information and the calculated ratio information match and be determined as abnormal if the existing ratio information and the calculated ratio information do not match.

Figure 5:
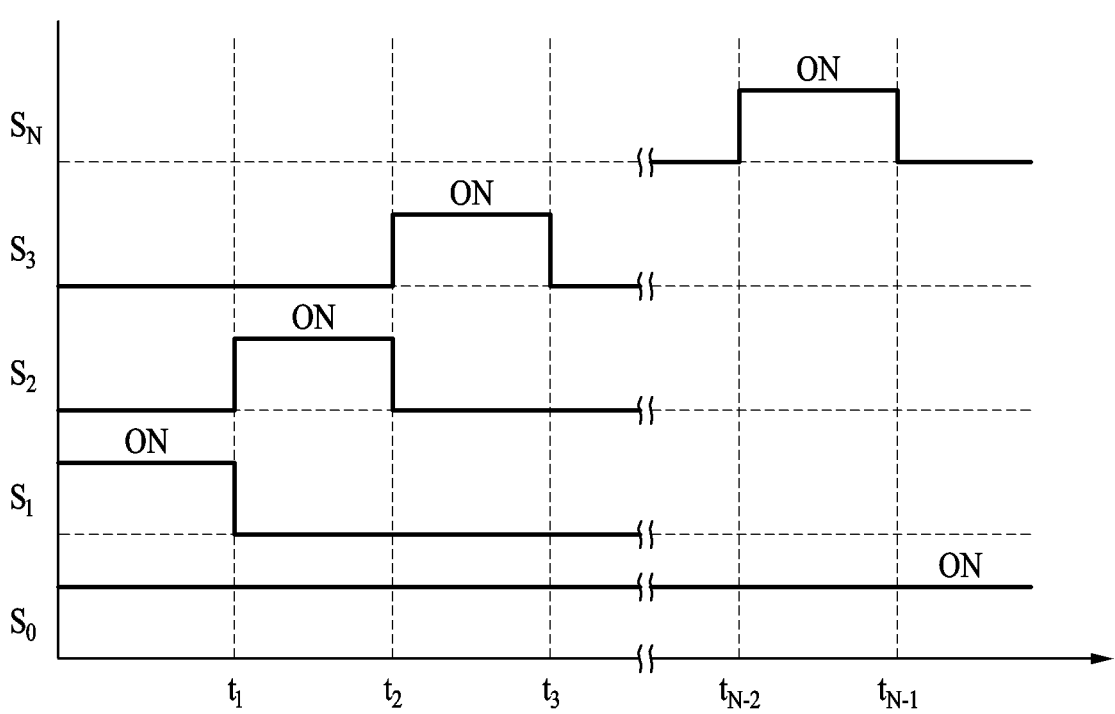
FIG. 5 is a diagram describing an order by which a radio wave signal is input to a radio wave signal comparator according to an example embodiment.

FIG. 5 is a diagram describing an order by which a radio wave signal is input to a radio wave signal comparator according to an example embodiment.

The operation and order of one period of an input of the radio wave signal comparator by the flow of time in an example embodiment of FIGS. 3 and 4 may be as illustrated in FIG. 5. The input of the radio wave signal comparator may be controlled by switches. The reference target radio wave signal So may be input to the radio wave signal comparator during the entire period, and the rest of the target radio wave signals except the reference target radio wave signal may be sequentially input in the current period. That is, only the target radio wave signal $S_1$ may be selected to be input to the radio wave signal comparator during time $t_1$, and only the target radio wave signal $S_2$ may be selected to be input to the radio wave signal comparator during $-_2$-$t_1$, and only the target radio wave signal $S_3$ may be selected to be input to the radio wave signal comparator during $-_3$-$t_2$. Sequentially proceeding in such a way, only the target radio wave signal SN may be selected during $t_{N-1}$-$t_{N-2}$ to be input to the radio wave signal comparator. The period may be repeatedly performed during the operation of the heat treatment device, with the input of all N–1 target radio wave signals to the radio wave signal comparator as one period.

Figure 6:
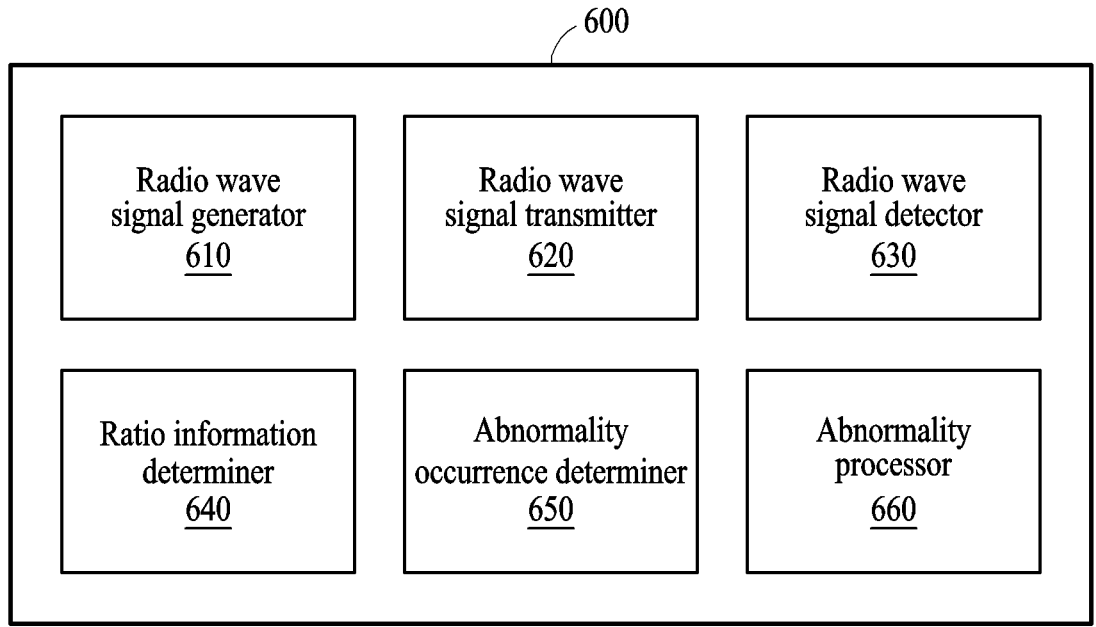
FIG. 6 is a diagram illustrating a configuration of a heat treatment device according to an example embodiment.

FIG. 6 is a diagram illustrating a configuration of a heat treatment device according to an example embodiment.

Referring to FIG. 6, the heat treatment device 600 may include a radio wave signal generator 610, a radio wave signal transmitter 620, a radio wave signal detector 630, a ratio information determiner 640, and an abnormality occurrence determiner 650. The heat treatment device 600 may further include a radio wave signal selector (not shown). Here, the heat treatment device 600 according to an example embodiment may correspond to the heat treatment device described herein. The heat treatment device 600 may include both an abnormality-detecting module and a heat treatment module, or include one of the abnormality-detecting module and a heat treatment module while the other one is connected. For example, the abnormality-detecting module may exist outside the heat treatment device 600 in a form of being connected to the heat treatment device 600 as an abnormality-detecting apparatus.

Referring to FIG. 6, the radio wave signal generator 610 may generate target radio wave signals for heat treatment. The radio wave signal generator 610 may generate the target radio wave signals by generating the initial radio wave signal, dividing the initial radio wave signal into a plurality of radio wave signals, controlling the signal phase and signal strength of each of the plurality of radio wave signals, and amplifying the radio wave signals having the adjusted signal phase and the adjusted signal strength.

The radio wave signal transmitter 620 may include an antenna which transmits the target radio wave signals to the human body. The radio wave signal detector 630 may detect the target radio wave signals from the antenna. The radio wave signal selector (not shown) may sequentially transmit the target signal radio waves detected by the radio wave signal detector 630 to the ratio information determiner 640. The radio wave signal selector (not shown) may correspond to the radio wave signal selector and the switch described herein.

The ratio information determiner 640 may compare the reference target radio wave signal included in the detected target radio wave signals and the rest of the target radio wave signals to determine the ratio information about the signal phase and the signal strength. The ratio information determiner 640 may compare the reference target radio wave and each of the rest of the target radio wave signals sequentially. The each of the rest of the target radio wave signals may be compared with the reference target radio wave signal by switches. The ratio information determiner 640 may calculate the ratio information about the signal phase and signal strength based on the signal phase and the signal strength of the reference target radio wave and the signal phase and the signal strength of the rest of the target radio wave signals. The ratio information determiner 640 may divide the reference target radio wave signal into a first reference target radio wave signal and a second reference target radio wave signal, shift a signal phase of the second reference target radio wave signal, calculate a first difference value which is a difference value between a half-wave signal phase and signal strength of the first reference target radio wave signal and a first half-wave signal phase and signal strength of the other target radio wave signals, calculate a second difference value which is a difference value between a half-wave signal phase and signal strength of the second reference target radio wave signal and a second half-wave signal phase and signal strength of the rest of the target radio wave signals, and calculate the ratio information based on the first difference value and the second difference value.

The abnormality occurrence determiner 650 may determine whether an abnormality occurs in the heat treatment device 600 based on the determined ratio information and the predetermined reference ratio information. If it is determined that the ratio information matches the existing ratio information based on the predetermined criteria, the abnormality occurrence determiner 650 may determine that an abnormality did not occur in the heat treatment device 600. If it is determined that the ratio information does not match the existing ratio information based on the predetermined criteria, the abnormality occurrence determiner 650 may determine that an abnormality occurred in the heat treatment device 600.

The heat treatment device 600 may further include an abnormality processor 660. The abnormality processor 660 may correct the signal strength and the signal phase of the target radio wave signals if it is determined that an abnormality occurred. Or the abnormality processor 660 may provide an alarm to notify the occurrence of the abnormality to the heat treatment device 600 and stop the operation of the heat treatment if it is determined that an abnormality occurred.

In one example embodiment, the operations performed by the radio wave signal generator 610, the radio wave signal transmitter 620, the radio wave signal detector 630, the ratio information determiner 640, the abnormality occurrence determiner 650, the radio wave signal selector, and the abnormality processor 660 included in the heat treatment device 600 may be performed by an apparatus which includes a processor (not shown) and a memory (not shown). The memory may store information necessary for the processor to execute processing. For example, the memory may store instructions executable by the processor, a radio wave signal, and the like. The memory may include a volatile memory such as a RAM, a DRAM, and a SRAM and/or a non-volatile memory known in the art such as a flash memory.

The processor may control the overall operation of the heat treatment device 600. The processor may include one or a plurality of processors, and the processor may include a general-purpose processor such as a central processing unit (CPU), an application processor (AP), and a digital signal processor (DSP), or a neural processing unit (NPU). In one example embodiment, the processor may execute the instructions stored in the memory so that the operations of the heat treatment device disclosed herein are performed.

The components described in the example embodiments may be implemented by hardware components including, for example, at least one DSP, a processor, a controller, an application-specific integrated circuit (ASIC), a programmable logic element, such as a field programmable gate array (FPGA), other electronic devices, or combinations thereof. At least some of the functions or the processes described in the example embodiments may be implemented by software, and the software may be recorded on a recording medium. The components, the functions, and the processes described in the example embodiments may be implemented by a combination of hardware and software.

The above-described devices may be configured to act as one or more software modules in order to perform the operations of the above-described examples, or vice versa.

As described above, although the examples have been described with reference to the limited drawings, a person skilled in the art may apply various technical modifications and variations based thereon. For example, suitable results may be achieved if the described techniques are performed in a different order and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. A heat treatment device comprising:
a processor configured to generate target radio wave signals for heat treatment; and
a radio wave signal transmitter comprising an antenna which transmits the target radio wave signals to a body of a user,
wherein the processor is configured to:
detect the target radio wave signals from the antenna;
determine ratio information about a signal phase and a signal strength by comparing a reference target radio wave signal included in the detected target radio wave signals and each of the other target radio wave signals; and
determine whether an abnormality occurs in the heat treatment device based on the determined ratio information and predefined reference ratio information,
wherein the processor is configured to:
divide the reference target radio wave signal into a first reference target radio wave signal and a second reference target radio wave signal;
shift a signal phase of the second reference target radio wave signal;
calculate a first difference value which is a difference value between a half-wave signal phase and signal strength of the first reference target radio wave signal and a first half-wave signal phase and signal strength of the other target radio wave signals;
calculate a second difference value which is a difference value between a half-wave signal phase and signal strength of the second reference target radio wave signal and a second half-wave signal phase and signal strength of the other target radio wave signals; and
calculate the ratio information based on the first difference value and the second difference value.

2. The heat treatment device of claim 1, wherein the processor is configured to:
generate an initial radio wave signal;
distribute the initial radio wave signal into a plurality of radio wave signals;
adjust a signal phase and a signal strength of each of the plurality of radio wave signals; and
generate the target radio wave signals by amplifying the radio wave signals having the adjusted signal phase and the adjusted signal strength.

3. The heat treatment device of claim 1, wherein the processor is configured to determine that an abnormality does not occur in the heat treatment device if it is determined that the ratio information matches reference ratio information based on a predetermined reference.

4. The heat treatment device of claim 1, wherein the processor is configured to determine that an abnormality occurs if it is determined that the ratio information does not match reference ratio information based on a predetermined reference.

5. The heat treatment device of claim 1, wherein the processor is configured to correct a signal strength and a signal phase of the target radio wave signals if it is determined that the abnormality occurs.

6. The heat treatment device of claim 1, wherein the processor is configured to provide an alarm for notifying about an occurrence of the abnormality of the heat treatment device and stop an operation of the heat treatment if it is determined that the abnormality occurs.

7. The heat treatment device of claim 1, wherein the target radio wave signals comprise a plurality of radio waves which are controlled to different signal phases and signal strengths.

8. The heat treatment device of claim 1, wherein the processor is configured to sequentially transmit the target radio wave signals which are detected by a radio wave signal detector to a ratio information determiner.

9. The heat treatment device of claim 1, wherein the processor is configured to sequentially compare the reference target radio wave and each of the other target radio wave signals,
wherein each of the other target radio wave signals is compared with the reference target radio wave signal by switches.

10. A method of detecting an abnormality of a heat treatment device, the method comprising:
generating target radio wave signals for heat treatment;
detecting the target radio wave signals from an antenna which transmits the target radio wave signals to a body;
determining ratio information about a signal phase and a signal strength by comparing a reference target radio wave signal included in the detected target radio wave signals and each of the other target radio wave signals; and
determining whether an abnormality occurs in the heat treatment device based on the determined ratio information and predefined reference ratio information,
wherein determining the ratio information comprises:
dividing the reference target radio wave signal into a first reference target radio wave signal and a second reference target radio wave signal;
shifting a signal phase of the second reference target radio wave signal;
calculating a first difference value which is a difference value between a half-wave signal phase and signal strength of the first reference target radio wave signal and a first half-wave signal phase and signal strength of the other target radio wave signals;
calculating a second difference value which is a difference value between a half-wave signal phase and signal strength of the second reference target radio wave signal and a second half-wave signal phase and signal strength of the other target radio wave signals; and
calculating the ratio information based on the first difference value and the second difference value.

11. The method of claim 10, wherein the generating of the target radio wave signals comprises:
generating an initial radio wave signal;
distributing the initial radio wave signal into a plurality of radio wave signals;
adjusting a signal phase and a signal strength of each of the plurality of radio wave signals; and generating the target radio wave signals by amplifying the radio wave signals having the adjusted signal phase and the adjusted signal strength.

12. The method of claim 10, wherein the determining of whether an abnormality occurs in the heat treatment device comprises determining that an abnormality does not occur in the heat treatment device if it is determined that the ratio information about the signal phase and the signal strength of the target radio wave signals matches reference ratio information based on a predetermined reference.

13. The method of claim 10, wherein the determining of whether an abnormality occurs in the heat treatment device comprises determining that an abnormality occurs if it is determined that the ratio information about the signal phase and the signal strength of the target radio wave signals does not match reference ratio information based on a predetermined reference.

14. The method of claim 10, further comprising correcting a signal strength and a signal phase of the target radio wave signals if it is determined that the abnormality occurs.

15. The method of claim 14, further comprising providing an alarm for notifying the abnormality of the heat treatment device and stopping the operation of the heat treatment if it is determined that the abnormality occurs.

16. The method of claim 10, wherein the determining of the ratio information comprises:

sequentially comparing the reference target radio wave and each of the other target radio wave signals, wherein each of the other target radio wave signals is compared with the reference target radio wave signal by switches.

\* \* \* \* \*